United States Patent
Brewer et al.

(10) Patent No.: US 10,694,995 B2
(45) Date of Patent: Jun. 30, 2020

(54) DIAGNOSTIC EYE GOGGLE SYSTEM

(71) Applicant: Renegade OptoPhysics LLC, Centennial, CO (US)

(72) Inventors: Michael A. Brewer, Centennial, CO (US); Shannon Rose Hinkley, Centennial, CO (US)

(73) Assignee: Renegade OptoPhysics, LLC, Centennial, CO (US)

( * ) Notice: Subject to any disclaimer, the term of this patent is extended or adjusted under 35 U.S.C. 154(b) by 142 days.

(21) Appl. No.: 15/832,233

(22) Filed: Dec. 5, 2017

(65) Prior Publication Data

US 2019/0167191 A1 Jun. 6, 2019

(51) Int. Cl.

| | |
|---|---|
| *A61B 5/00* | (2006.01) |
| *A61B 3/10* | (2006.01) |
| *A61F 9/02* | (2006.01) |
| *A61B 3/113* | (2006.01) |
| *G02B 27/01* | (2006.01) |
| *A61B 5/024* | (2006.01) |
| *A61B 3/12* | (2006.01) |

(52) U.S. Cl.
CPC .......... *A61B 5/6803* (2013.01); *A61B 3/1015* (2013.01); *A61B 3/113* (2013.01); *A61F 9/029* (2013.01); *A61B 3/1233* (2013.01); *A61B 5/02416* (2013.01); *G02B 2027/0178* (2013.01)

(58) Field of Classification Search
None
See application file for complete search history.

(56) References Cited

U.S. PATENT DOCUMENTS

| | | |
|---|---|---|
| 5,140,990 A | 8/1992 | Jones et al. |
| 6,236,047 B1 | 5/2001 | Malin et al. |
| 6,305,804 B1 | 10/2001 | Rice et al. |
| 6,575,574 B2 | 6/2003 | DellaVecchia et al. |
| 7,140,730 B2 | 11/2006 | Wei et al. |
| 7,336,982 B2 | 2/2008 | Yoo |
| 7,641,343 B1 | 1/2010 | Motamedi et al. |
| 7,828,438 B1 | 11/2010 | Motamedi et al. |
| 8,474,978 B2 | 7/2013 | Huang et al. |
| 8,494,606 B2 | 7/2013 | Debreczeny et al. |
| 8,632,262 B2 | 1/2014 | Delianides et al. |
| 8,649,008 B2 | 2/2014 | Kashani et al. |
| 8,740,381 B2 | 6/2014 | Youssefi et al. |

(Continued)

*Primary Examiner* — William R Alexander
*Assistant Examiner* — Gary W O'Neill
(74) *Attorney, Agent, or Firm* — Williams Intellectual Property; Timothy Snyder (57) ABSTRACT

A diagnostic eye goggle system is described herein. The diagnostic eye goggle system includes goggles having a radiation source, a radiation sensor, optical elements, and a microcontroller for acquiring optical data from a user's eye including, but not limited to, wavefront data, spectral data, and frequency-shifted wavelength data. An external master database stores historical user data from previous users of the diagnostic eye goggle system. A transceiver disposed in the goggles provides a datalink between the acquired optical data and the external master database. A diagnostic software module cross-correlates the acquired optical data with the historical data to provide a diagnosis of a disease state of the user. The goggles further provide lens-correcting instructions or suggestions to a user or health care provider based on the acquired wavefront data.

19 Claims, 5 Drawing Sheets

(56) References Cited

U.S. PATENT DOCUMENTS

| | | |
|---|---|---|
| 2005/0267343 A1 | 12/2005 | Woods et al. |
| 2011/0082355 A1 | 4/2011 | Eisen et al. |
| 2015/0038810 A1 | 2/2015 | Melker |
| 2015/0313462 A1 | 11/2015 | Reis |
| 2017/0000324 A1* | 1/2017 | Samec .................. A61B 3/102 |
| 2017/0311796 A1* | 11/2017 | Walsh .................. A61B 3/102 |
| 2019/0307350 A1* | 10/2019 | Sridhar ................ A61B 5/4088 |
| 2019/0380875 A1* | 12/2019 | Esmonde ............... A61B 3/113 |
| 2020/0030150 A1* | 1/2020 | Oduncu ............... A61B 5/6803 |

* cited by examiner

DIAGNOSTIC EYE GOGGLE SYSTEM

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Human body diseases are triggered by a multitude of potential triggering events including environmental pressures, physiological changes, or genetically induced causes, to name a few. The detection of a disease, or disease onset, is paramount to the health of the population and has been an evolving field in modern medicine. One of the more effective methods for detecting a disease is through blood tests. However, recent advances in optics and signal processing have given rise to several non-invasive diagnostic techniques to detect diseases. The non-invasive diagnostic techniques primarily rely on electromagnetic radiation. Based on how the radiation interacts with bodily tissues or analytes, an indication of the presence or absence of a disease state (e.g., cancer, liver disease) can be determined. Various non-invasive diagnostic techniques are known in the prior art; however many techniques provide very limited information about the overall health of the patient. The current non-invasive diagnostic techniques often utilize clunky benchtop devices that are primarily focused on the detection of a single blood analyte, the monitoring of volumetric changes of tissue structures (e.g., plethysmography), or the oxygenation levels of the blood (e.g., pulse oximetry), which are usually directed to the diagnosis or monitoring of a specific disease state. In addition, the current techniques do not provide information about the presence or absence of non-tested diseases, whether the patient experienced a disease triggering event, or the severity of a disease (i.e., disease stage).

Thus, there is a need in the art for a diagnostic eye goggle system capable of collecting and analyzing multiple types of optical data from a user's eye and cross correlate that data with historical data to identify one or more disease states of the user. There is a further need for a diagnostic eye goggle system capable of tracking the biological and physical changes in the eye of a user with or without a disease, and use the tracked changes to identify one or more disease states of a future user.

FIELD OF THE INVENTION

The present invention relates to a diagnostic eye goggle system, and more particularly, to a diagnostic eye goggle system utilizing optical measurements of a user's eye and a master database having historical user data to identify a disease state of the user or provide lens-correcting suggestions.

SUMMARY OF THE INVENTION

The general purpose of the diagnostic eye goggle system, described subsequently in greater detail, is to provide a diagnostic eye goggle system which has many novel features that result in a diagnostic eye goggle system which is not anticipated, rendered obvious, suggested, or even implied by prior art, either alone or in combination thereof.

A diagnostic eye goggle system is provided to identify a disease state of a user and detect eye aberrations for corrective lensing. The eye goggles system generally includes goggles and an external master database having historical user data. The goggles include a front frame situated in front of the user's eyes when the goggles are worn about the user's head. The front frame includes one or more electromagnetic radiation sources disposed to emit radiation into one or more eyes of the user. One or more radiation sensors disposed to detect at least one of refraction, reflection, interference, frequency-shift, intensity, wavefront, or a spectrum of reflected radiation reflected from one or more structures in the user's eye. One or more optical elements disposed between the radiation source and the radiation sensor for manipulating at least one of the emitted radiation and the reflected radiation. A microcontroller disposed in communication with at least one of the electromagnetic radiation source, the radiation sensor, or the optical elements, said microcontroller coordinating the emission of radiation into the user's eye and analyzing data received from the radiation sensors. And, a transceiver disposed in communication with the microcontroller, said transceiver data linking the microcontroller with the external master database to permit the transmission of data therebetween, wherein a diagnostic software module cross-correlates the analyzed data from the microcontroller with the historical user data in the master database to identify the disease state of the user.

The microcontroller further includes a processor and memory. The memory includes three or more optical data modules stored therein. The modules have software executable instructions that when executed by the processor causes the processor to acquire three or more different types of optical data from the eye. A first optical data acquisition module that when executed by the processor causes the processor to: command at least one of the radiation source and optical elements to emit one or more pulses of radiation onto the retina of the user's eye, wherein a wavefront of reflected radiation is detected by the sensor and transferred to the microcontroller for eye aberration analysis. A second optical data acquisition module when executed by the processor causes the processor to: command at least one of the radiation source and optical elements to emit one or more pulses of a continuous radiation spectrum on one or more blood vessels in the user's eye, wherein a spectrum of the reflected radiation is detected by the sensor and transferred to the microcontroller for at least one of analyte or structure analysis of the eye. A third optical data acquisition module when executed by the processor causes the processor to: command at least one of the radiation source and optical elements to emit one or more specific wavelengths of radiation on one or more structures of the retina, wherein a frequency-shifted wavelength of reflected light is detected by the sensor and transferred to the microcontroller for at least one of analyte or structure analysis of the eye.

The microcontroller further generates a mathematical map of the eye, said map having map data corresponding to an analyzed wavefront, an analyzed spectra of reflected radiation, and an analyzed frequency-shift of reflected radiation, wherein the mathematical map of the eye is transferred and stored in the master database and the diagnostic software module compares the mathematical map of the eye with historical user's mathematical maps to identify a disease state of the user. The map data corresponding to the analyzed wavefront may be comprised of Zernike Polynomials. The map data corresponding to the analyzed spectra of reflected radiation may comprise one or more spectral line fingerprints associated with one or more blood analyte spectral line fingerprints.

The master database may further receive and stores medical history data of the user that is linked to the user's mathematical map. The diagnostic software module then cross-correlates a present user's mathematical map with a historical user's mathematical map to identify a statistical match therebetween, and subsequently diagnose the disease state of the present user based on the medical history of a matched historical user.

The one or more electromagnetic radiation sources include at least one of a light emitting diode (LED), a solid-state laser, or incandescent light bulb that can emit radiation in the range of 380 nanometers in wavelength to 2500 nanometers in wavelength. The one or more radiation sensors is at least one of a charged-coupled device (CCD) sensor, a Hartmann-Shack wavefront sensor, or an array of photodiodes. The one or more optical sensors include at least one of a slit, a pinhole, a collimator, a mirror, a beam-splitter, a lens, an x-y scanner, an x-y-z scanner, a prism, a reference arm, or a combination thereof.

A method for diagnosing a disease state of a user with the eye goggle system is also provided. The method includes assembling the goggles about the user's head wherein the front panel is situated in front of the user's eyes. Emitting a first set of radiation on the user's retina with the radiation source. Detecting and collecting a wavefront of reflected radiation reflected from the user's retina with the sensor. Emitting a second set of radiation on the user's retina with the radiation source. Detecting and collecting a spectrum of reflected radiation reflected from the user's retina with the sensor. Emitting a third set of radiation on the user's retina with the radiation source. Detecting and collecting a wavelength of reflected radiation reflected from the user's retina with the sensor. Generating a mathematical map of the eye based on the wavefront, spectrum, and wavelength of the reflected radiation. Transmitting and storing the mathematical map of the eye to a master database for diagnosing future users of the goggles. And, cross-correlating the mathematical map of the eye with historical user's mathematical maps to identify a disease state of the user or provide lens-correcting instructions to the user. The method may further include repeating the aforementioned steps at several time points for a user having a particular disease to track and store the changes of the mathematical map as a function of disease progression or regression.

Thus has been broadly outlined the more important features of the present disease detecting eye goggle system so that the detailed description thereof that follows may be better understood and in order that the present contribution to the art may be better appreciated.

Objects of the present disease detecting eye goggle system, along with various novel features that characterize the invention are particularly pointed out in the claims forming a part of this disclosure. For better understanding of the disease detecting eye goggle system, its operating advantages and specific objects attained by its uses, refer to the accompanying drawings and description.

BRIEF DESCRIPTION OF THE DRAWINGS

Figures

FIGS. 4A-4D depict different types of optical data acquired by the goggles, where

DETAILED DESCRIPTION OF THE DRAWINGS

The present invention has utility as a diagnostic eye goggle system to acquire optical data from a user's eye and cross-correlate the optical data with historical optical data to identify at least one of a disease state or a disease stage of the user. The diagnostic eye goggle system has additional utility in providing lens-correcting instructions or suggestions to the user or health care provider. The following description of various embodiments of the invention is not intended to limit the invention to those specific embodiments, but rather to enable any person skilled in the art to make and use this invention through exemplary aspects thereof. It will be clear and apparent to one skilled in the art that the invention can be adapted to diagnose several diseases, disease states, and disease stages illustratively including: cancer; organ disease (e.g., liver, heart, brain, skin); nerve and vessel disease; bacterial, parasite and viral infections; and eye diseases (e.g., glaucoma, macular degeneration).

It is to be understood that in instances where a range of values are provided that the range is intended to encompass not only the end point values of the range but also intermediate values of the range as explicitly being included within the range and varying by the last significant figure of that range. By way of example, a recited range of 1 to 4 is intended to include 1-2, 1-3, 2-4, 3-4, and 1-4.

With reference now to the drawings, and in particular FIGS. 1 through 6 thereof, examples of the instant diagnostic eye goggle system employing the principles and concepts of the present diagnostic eye goggle system and generally designated by the reference number 10 will be described.

Figure 1:
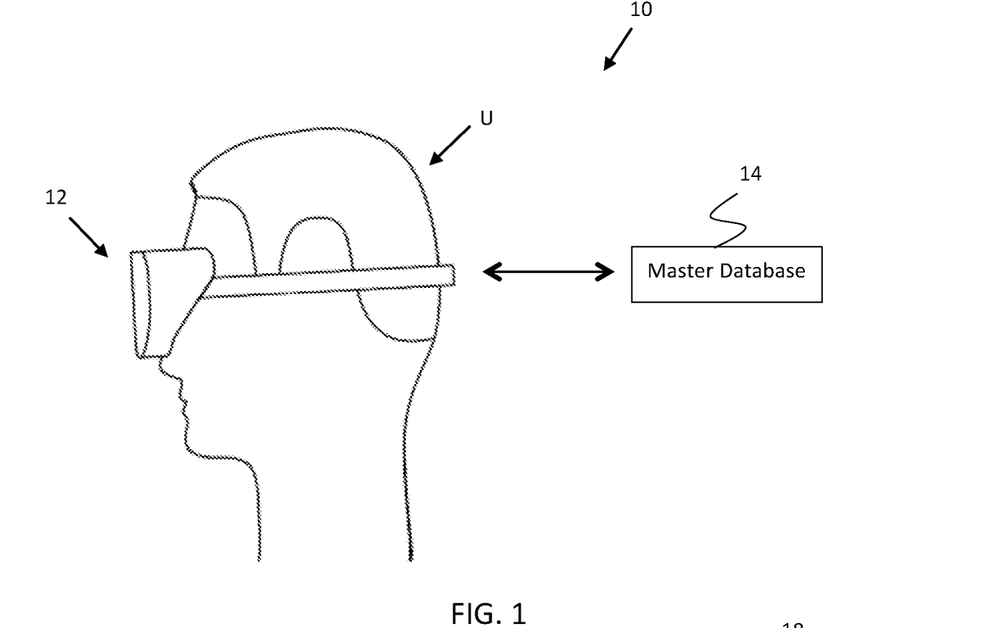
FIG. 1 depicts a diagnostic eye goggle system having a user wearing goggles that interface with an external master database.
Figure 2:
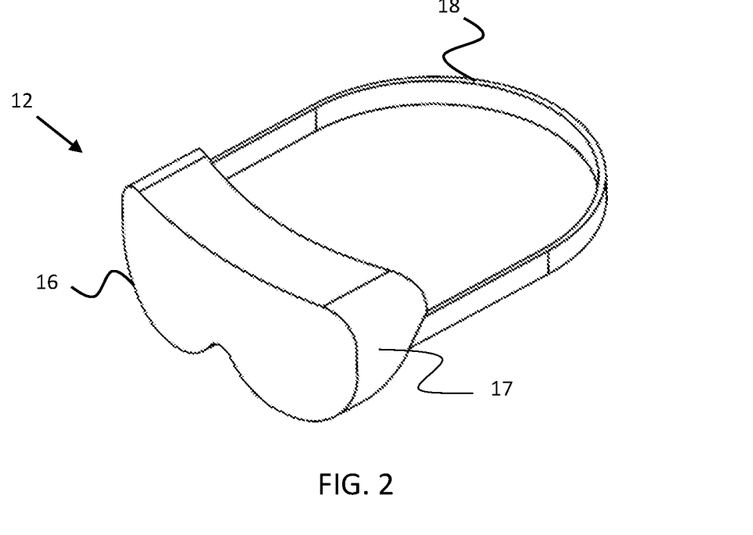
FIG. 2 is a perspective view of the goggles.

With reference to FIGS. 1 and 2, particular embodiments of the general components of the present diagnostic eye goggle system 10 is illustrated. The diagnostic eye goggle system 10 generally includes goggles 12 and an external master database 14. The external master database 14 includes data from historical users of the goggles 12, referred to herein as historical user data. In specific embodiments, the external master database 14 is stored on or more servers and accessible by an Internet connection, however, it should be appreciated that the external master database 14 may be stored on a private server or intranet and may be accessible by other wired or wireless connections. The goggles 12 generally include a front panel 16 and a head securement feature 18. The front panel 16 is situated in front of the user's eyes when the goggles are worn about the user's head (U). In a particular embodiment, the front panel 16 includes a light shield 17 around the front panel 16 that conforms about the user's eyes to eliminate exposure of natural light to the user's eyes. The light shield 17 may project around an outer edge of the front panel 16 to make contact with the user's face. The light shield 17 may further be made of a flexible, and light absorbent material. The head securement feature 18 is configured to secure the goggles 12 to the user's head (U). The securement feature 18 may include an elastic strap, an adjustable strap, temples that fit on the user's ears, a nose clip that assembles to the user's nose, and equivalents thereof.

Figure 3:
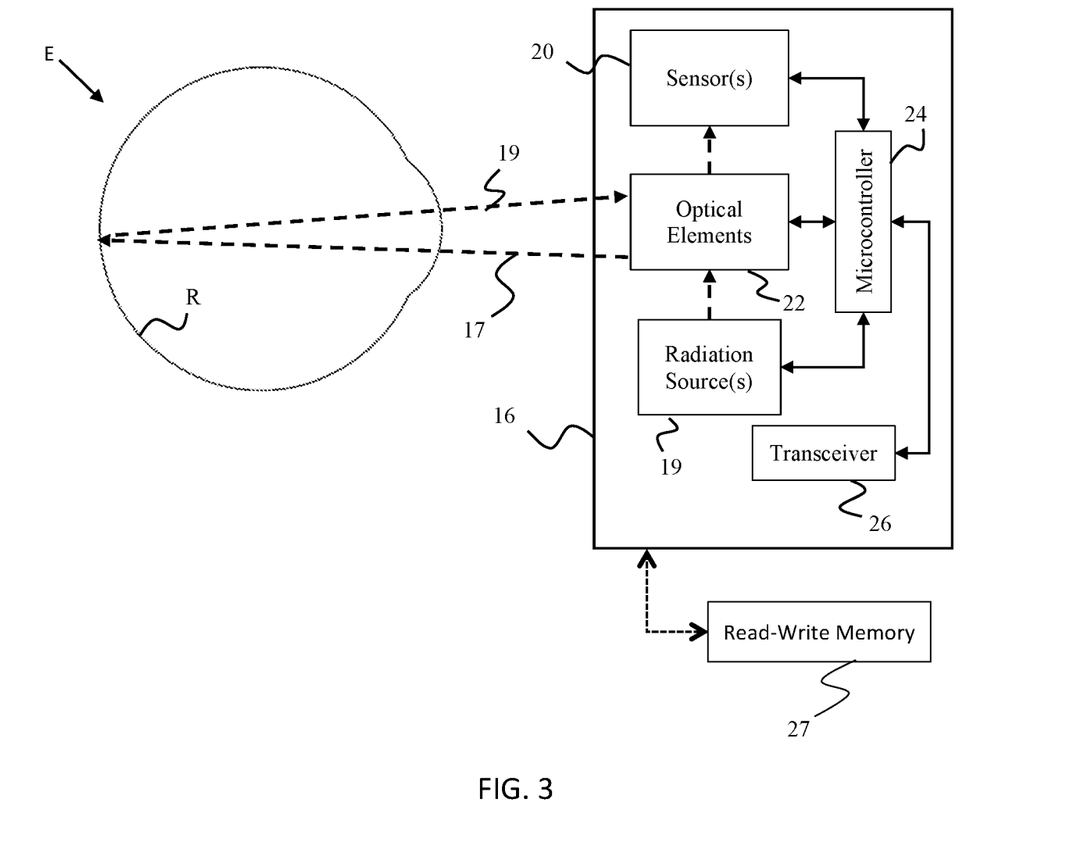
FIG. 3 depicts the components of the goggles and how the goggles interact with a user's eye.

With reference to FIG. 3, a particular embodiment of the front panel 16 of the goggles 12 is shown in the context of emitting and receiving radiation (denoted as the dashed arrows 17 and 19, respectively) into and out of a user's eye (E). The front panel 16 includes a plurality of components to acquire optical data from the user's eye (E). The front panel 16 may include one or more electromagnetic radiation sources 19 disposed to emit radiation into one or more eyes (E) of the user. The radiation source(s) 19 may include one or more light emitting diodes (LEDs), solid-state lasers, incandescent light, fluorescent light, or a combination thereof. The radiation source(s) are configured to emit radiation having minimal harmful effects on the structures of the eye (E). In a specific embodiment, the emitted radiation wavelength may range from 380 nanometers in wavelength to 2500 nanometers in wavelength corresponding to the visible and infrared spectrum of radiation. In some embodiments, the emitted radiation has a shorter wavelength below 380 nanometers but greater than 50 nanometers.

The front panel 16 further includes one or more radiation sensors 20 to detect at least one of refraction, reflection, interference, intensity, frequency-shift, wavefront, or a spectrum of reflected radiation reflected from one or more structures in the user's eye (E). The radiation sensors 20 may include a charged-coupled device (CCD) sensor, a Hartmann-Shack wavefront sensor, or an array of photodiodes.

The front panel 16 may further include one or more optical elements 22 disposed between the radiation source and the radiation sensor for manipulating at least one the emitted radiation and the reflected radiation. The one or more optical sensors may include at least one of a slit, a pinhole, a collimator, a mirror, a beam-splitter, a lens, an x-y scanner, an x-y-z scanner, a prism, a reference arm, or a combination thereof. In another embodiment, the radiation emitted from the radiation source(s) 19 is directly detected by the radiation sensor(s) 20 without the use of the optical elements 22. However, it should be appreciated that a simple slit or pinhole disposed in front of the radiation source 19 may be regarded as an optical element 22.

The front panel 16 further includes a microcontroller 24 disposed in communication with at least one of the radiation source 19, the radiation sensor 20, and optical elements 22. The microcontroller 24 generally coordinates the emission of radiation into the user's eye(s) (E) and analyzes the data received from the radiation sensor(s) 20. The microcontroller 24 further includes a processor and memory. A transceiver 26 is further disposed in communication with the microcontroller 24. The transceiver 26 provides a datalink between the microcontroller 24 and the external master database 14. The interface may be accomplished with a wired or wireless connection including Ethernet cables, BUS cables, a power line, Bluetooth, Wi-Fi, radiofrequency, and equivalents thereof. In addition, the datalink may be accomplished through a wired or wireless network, illustratively including, a local area network, or the Internet. Further, the term "in communication" refers to a wired or wireless connection between two or more stated elements (e.g., microcontroller 24 and transceiver 26) and does not necessarily require a direct one-to-one connection where other elements (e.g., circuitry, a network) may facilitate or be part of the connection between the two or more stated elements.

The diagnostic eye goggle system 10 further includes a diagnostic software module that cross-correlates analyzed data from the microcontroller with the historical data in the master database 14 to identify a disease state of the user. In one embodiment, the diagnostic software module is stored in memory associated with the microcontroller 24 and executed by a processor of the microcontroller 24. In another embodiment, the diagnostic software module is stored in memory associated with the master database 14 and executed by a processor associated with the master database 14. The diagnostic software module may use several algorithms for identifying a statistical match, illustratively including: a) running the analyzed data through a decision tree to classify the analyzed data into a cohort and subsequently comparing the analyzed data to historical data within said cohort; b) comparing one or more finite outputs from the analyzed data (e.g., Zernike Polynomials) with one or more outputs associated with the historical user data; c) Naïve Bayes classifiers to recognize specific patterns in the analyzed data and match the specific patterns with patterns associated with the historical user data; d) regression analysis to correlate how the analyzed set of data statistically compares to historical user's data; and e) clustering algorithms to cluster the analyzed set of data with historical user data to aid in finding a statistical match. In some embodiments, the diagnostic software module iteratively compares the analyzed data from the microcontroller 24 with historical analyzed data from each historical user of the diagnostic eye goggle system 10. For example, if the master database 14 includes historical analyzed data from 5,000 users, then the diagnostic software module compares the present analyzed user's data with each of the 5,000 previous user's analyzed data to identify a match. In other embodiments, the optical data from the 5,000 historical users are classified into one or more groups, which may or may not correspond to a particular disease, disease state, or disease stage. The present user's analyzed data is then first grouped or classified into one or more groups and subsequently compared with each of the historical user's data in said group. Specific types of optical data to be acquired, analyzed, and matched are further described below.

In specific inventive embodiments, the diagnostic eye goggle system 10 further includes read-write memory 27 for performing offline tasks when the eye goggles 12 are disconnected from the master database 14. In one embodiment, the read-write memory 27 is housed in the front panel 16 and disposed in communication with the microcontroller 24. In another embodiment, the read-write memory 27 is external to the goggles 12 but in communication with the microcontroller 24 and in the same locational vicinity as the goggles 10, such as an external hard drive, universal serial bus (USB) drive, and equivalents thereof. While in other embodiments, the read-write memory 27 is the same as the aforementioned memory associated with the microcontroller 24. The read-write memory 27 is particularly advantageous as the memory 27 permits the goggles 12 to function without connectivity to the master database 14. For example, the goggles 12 may be sent to a remote African village to acquire optical eye data from remote users in the local population. The read-write memory 27 may then store optical eye data from a plurality of remote user's in that local population. Once the goggles 10 are capable of re-connecting to the master database 14 (e.g., through an internet connection), the optical eye data from the plurality of user's are transferred and stored in the master database 14 and an identification of a disease state or disease stage for each individual may be provided.

In a particular inventive embodiment, the read-write memory 27 may further store historical user data to identify a disease state and/or stage without having to connect to the master database 14. The diagnostic software module may be stored in the read-write memory 27 and executed by the processor of the microcontroller 24 to identify a disease state and/or stage of the remote users. In some instances, the file size of the totality of the historical user data may be too large to store in the read-write memory 27. In such a case, a selected portion of the historical user data is stored in read-write memory 27. In a particular embodiment, the selected portion of the historical user data stored in the read-write memory 27 is selected based on a type of a disease and/or a prevalence of a disease. For example, the eye goggles 12 may be sent to an African village having an outbreak of malaria. Optical eye data from historical users having malaria is then selected as the portion of historical user data that is stored in the read-write memory 27. The eye goggles 12 are then equipped to quickly identify if any user's in the African village population has malaria without having to connect with the master database 14. In another example, the read-write memory 27 only stores common diseases, while keeping uncommon diseases stored in the master database 14. Therefore, the read-write memory 27 is not overloaded with historical user data and the computational time to cross-correlate and identify a disease is reduced. Then, once the goggles 12 re-connect with the master database 14, any uncommon diseases from the remote population may be identified.

With reference to FIGS. 4A through 4D, several types of optical data to be acquired and analyzed from the eye (E) are illustrated. In a particular embodiment, the memory associated with the microcontroller 12 stores three or more optical data acquisition modules. The three or more optical data acquisition modules include software executable instructions to acquire three or more different types of optical data from the eye (E). In a particular embodiment, with reference to FIG. 4A, a first optical data acquisition module is configured to identify eye aberrations by detecting the refraction of reflected radiation from the eye (E). The first optical data acquisition model includes instructions when executed by the processor causes the processor to: command at least one of the radiation source 19 and optical elements 22 to emit one or more pulses of radiation 28 onto the retina (R) of the user's eye (E), wherein a wavefront 30 of reflected radiation 32 is detected by the sensor 20 and transferred to the microcontroller 24 for eye aberration analysis. The radiation sensor 20 for detecting the wavefront 30 may be a Hartmann-Shack wavefront sensor having a lenslet array and a CCD sensor. In one embodiment, the lenslet array is part of the optical elements 22 and the CCD sensor is the radiation sensor 20. The eye aberration analysis may include the determination of the Zernike Polynomials from the detected refractions of radiation over the area of the eye (E). In other embodiments, the wavefront is acquired using Tscherning aberroscopy or ray tracing.

Figures 4A, 4B:
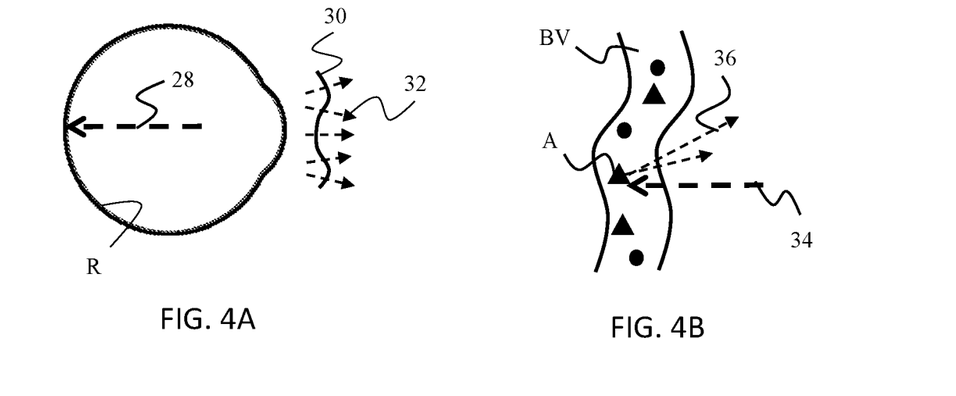
FIG. 4A depicts the detection of a wavefront.
FIG. 4B depicts the detection of analytes with spectral analysis.

With reference to FIG. 4B, a second optical data acquisition module is configured to identify the presence or absence of one or more analytes (A) in the blood vessels (BV) or other tissue structures of the user's eye (E). The second optical data acquisition module includes instructions when executed by the processor causes the processor to: command at least one of the radiation source 19 and optical elements 22 to emit one or more pulses of a continuous spectrum of radiation 34 on one or more blood vessels (BV) or tissue structures in the user's eye (E). A spectrum of the reflected radiation 36 is detected by the sensor 20 and transferred to the microcontroller 24 to analyze the presence, absence or concentration of an analyte (A) in the blood vessels (BV), tissues, or tissue structures in the user's eye (E). The continuous spectrum of emitted radiation 34 may be white light comprised of the visible light spectrum of radiation. The continuous spectrum may further include a spectrum of infrared light that may absorb, reflect, or interact with an analyte (A) in the blood vessel (BV), tissue, or tissue structure in the eye (E). The reflected light 36 is detected and analyzed to determine one or more spectral line fingerprints by examining at least one of: a) the presence or absence of a particular wavelength of light that reflected from the eye (E); and/or b) the intensity of a particular wavelength of light reflected from the eye (E). The optical elements 22 may include a prism to spread the reflected light 36 into their corresponding wavelengths for analysis. The spectral line fingerprints provide an indication of the presence, absence, or a concentration of a particular analyte (A) in the user's blood or other tissue structures in the user's eye (E). In a specific embodiment, the radiation source 19, optical elements 22, and sensors 20 may include components to employ Raman spectroscopy for obtaining a spectral analysis of one or more analytes in the eye (E).

Figure 4C:
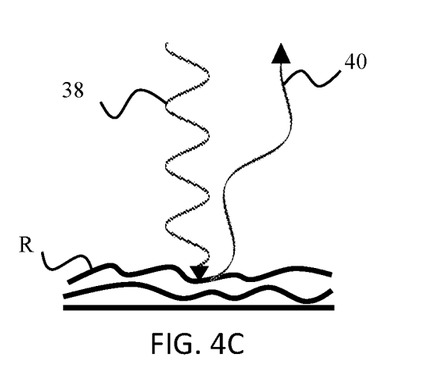
FIG. 4C depicts the detection of frequency-shifted radiation.

In a particular embodiment, with reference to FIG. 4C, a third optical data acquisition module is configured to detect a frequency-shift in emitted radiation 38 compared to the reflected radiation 40. As illustrated in FIG. 4C, the emitted radiation 38 has a shorter wavelength than the reflected radiation 40. The third optical data acquisition module when executed by the processor causes the processor to: command at least one of the radiation source 19 and optical elements 22 to emit one or more specific wavelengths of radiation 38 on one or more blood vessels (BV), tissues, or tissue structures in the eye (E), wherein a frequency-shifted wavelength of reflected radiation 40 is detected by the sensor and transferred to the microcontroller for at least one of analyte (A), tissue, or tissue structure analysis of the eye (E). For example, the microcontroller 24 may command the radiation source 19 and/or optical elements 22 to emit radiation 38 having a wavelength of 520 nm at a particular tissue structure or blood vessel (BV) in the eye (E), and detect a reflected wavelength 40 of 600 nm. The frequency-shift in the reflected radiation 40 indicates how the light interacted with the particular analyte (A), tissue, or tissue structure to ascertain the quality of a tissue or tissue structure and identify at least one of the presence, absence, or concentration of an analyte (A) in the eye (E).

Figure 4D:
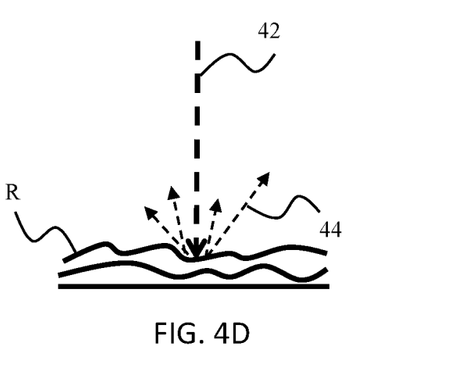
FIG. 4D depicts the detection of reflected radiation patterns on specific regions of the eye.

In a specific embodiment, with reference to FIG. 4D, a fourth optical data acquisition module is configured to detect an angular degree of reflected radiation reflected from one or more specific target locations on the retina (R) or other tissue structures in the eye (E). The fourth optical data acquisition module when executed by the processor causes the processor to: command at least one of the radiation source 19 and optical elements 22 to emit one or more pulses of radiation 42 at one or more target locations on the retina (R) or other structures in the eye (E), wherein an angular degree of reflected radiation 44 is detected by the sensor 20 and transferred to the microcontroller 24 to analyze a topography of the targeted location(s). Depending on the topography of the target location, the radiation may reflect in different directions due to an irregularly shaped surface. An irregular topographical surface of a target location may be indicative of a particular disease, disease state, or disease stage.

In a particular embodiment, a fifth optical data acquisition module is configured to emit one or more specific wavelengths of radiation and detect the intensity of reflected radiation. The fifth optical data acquisition module when executed by the processor causes the processor to: command at least one of the radiation source 19 and optical elements 22 to emit one or more pulses of one or more specific wavelengths of radiation, wherein an intensity, or amount of reflected radiation, is detected by the sensor 20 and transferred to the microcontroller 24 to analyze the presence, absence, or concentration of one or more analytes (A) in a blood vessel (A) or other tissue in the eye (E). For example, some analytes (A) may absorb radiation at a first wavelength (providing a low intensity reading), and reflect radiation at a second wavelength (providing a high intensity reading). The difference between the detected intensities of reflected radiation between the two different emitted wavelengths may be indicative of a concentration of a particular analyte (A). In a particular embodiment, the optical elements 22 may include a prism that is adjusted in response to commands by the microcontroller 24 to emit a specific wavelength. In other embodiments, the radiation source 19 includes a plurality of LEDs that may each emit a specific wavelength when commanded to do so.

In a specific inventive embodiment, a sixth optical data acquisition module is configured to detect one or more volumetric changes of a blood vessel (BV) or tissue structure in the eye (E). The sixth optical data acquisition module when executed by the processor causes the processor to: command at least one of the microcontroller 24 or optical elements 22 to emit a plurality of pulses of radiation on and around one or more blood vessels in the user's eye (E), wherein the sensor detects a change in the reflected radiation between pulses that corresponds to a volumetric change in one or more of the blood vessels. The sixth optical data acquisition module acts as a plethysmograph to monitor blood pressure, blood flow, and heart rate.

In a particular inventive embodiment, a seventh optical data acquisition module is configured to obtain images of surfaces and sub-surfaces of tissue structures in the eye (E). The seventh optical data acquisition module when executed by the processor cause the processor to: command at least one of the microcontroller 24 or optical elements 22 to emit a plurality of pulses of infrared radiation on one or more targeted tissue structures, wherein the sensor detects a reflectivity profile of the targeted tissue containing information about the spatial dimensions and location of tissue structures. The seventh optical data acquisition module is generally referred to as optical coherence tomography.

It should be appreciated, that the aforementioned tissues and tissue structures in the eye (E) illustratively include specific regions of the retina (R), the corneal tear film, the macula, the fovea, the vitreous body, the aqueous humor (fluid), the optical nerve, the lens, the pupil, the cornea, and ganglion cells. It should further be appreciated that the aforementioned analytes (A) to be detected in the blood vessels (BV) or tissues illustratively include, but not limited to: compounds such as glucose and bilirubin; enzymes such as amylase, lipase, aspartate transaminase, and alanine transaminase; metals such as mercury; cells such as white blood cells; and other proteins or metabolites such as growth factors and signaling proteins.

Figure 5:
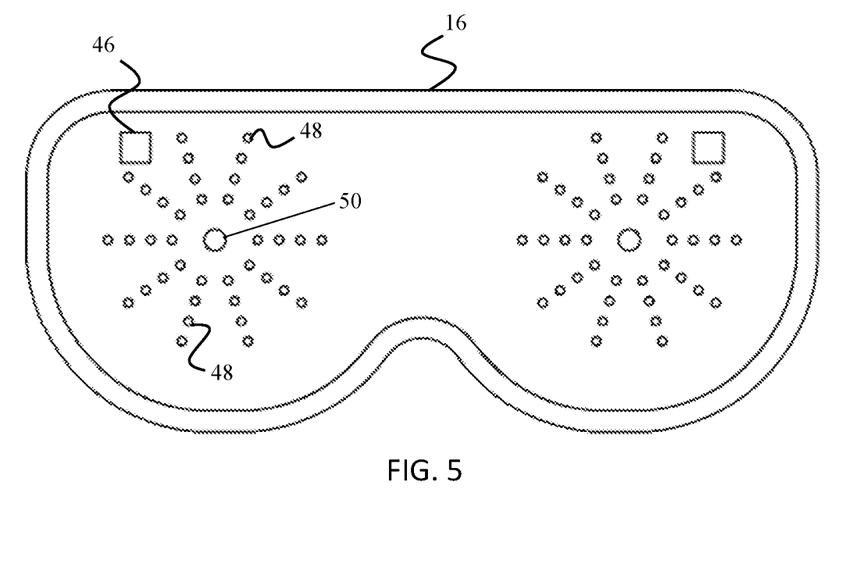
FIG. 5 depicts a front panel of the goggles having a camera and eye directing lights.

To direct the emitted radiation to detect analytes and/or abnormalities on specific regions of the eye (E), the front panel 16 may further include components for directing the emitted radiation. In one embodiment, the microcontroller 24 is disposed in communication with one or more optical elements 22 to actively manipulate at least one of the emitted radiation or the reflected radiation. The optical elements 22 may include one or more actuating components, illustratively including, servo-motors, step-motors, pivots, ball screws, nuts, linear rails, and equivalents thereof to actively adjust one or more of the optical elements 22 based on commands from the microcontroller 24 (e.g., an x-y scanner for directing the radiation at a plurality of pre-programmed locations). The three or more optical data acquisition modules when executed by the processor cause the processor to: actively direct the emitted radiation to a plurality of specific locations on the retina by actively adjusting one or more of the optical elements 22 (e.g., a mirror, a pinhole) with the actuating components. With reference to FIG. 5, the front panel 16 may further include a camera 46 disposed in communication with the microcontroller 24. The camera 46 includes an eye tracking software module for locating and tracking the pupil of the eye (E). Therefore, the emitted radiation may be actively and accurately directed to specific locations in the eye (E) based, in part, on a current position of the user's pupil.

With reference to FIG. 5, the radiation may be directed to specific regions on the eye using a plurality of eye directing lights 48. The front panel 16 may include a plurality of eye directing lights 48 situated about a radiation emission aperture 50 in the front panel 16. The eye directing lights 48 are shown in a radial pattern about the radiation emission aperture 50. The eye directing lights 48 are configured to direct the user's line-of-sight in a particular direction to collect optical data on a specific region in the eye (E). The three or more optical data acquisition modules may include additional instructions when executed by the processor cause the processor to: illuminate a sequence of the eye directing lights to sequentially direct the user's eye (E) to an illuminated light; command the radiation source to emit one or more pulses of radiation into the user's eye (E) for each position the eye (E) is directed to an illuminated light; and collect the reflected radiation reflected from the retina when the eye (E) is directed to each illuminated light. For example, to target a region of the eye (E) below the macula, an eye directing light 48 located below the radiation emission aperture 50 is illuminated directing the user's line-of-sight down. Thus, radiation emitted through the pupil will make contact with retinal structures located below the macula. The eye directing lights 48 may be used in lieu of optical elements 22 that actively direct emitted radiation at specific locations in the eye (E), or the eye directing lights 48 may be used in conjunction with optical elements 22 that actively direct emitted radiation.

During and/or after the optical data acquisition process, in specific embodiments, the microcontroller 24 generates a mathematical map of the eye (E) having map data corresponding to the analyzed data collected from the optical data acquisition modules. The map data may includes one or more analyzed wavefronts, one or more analyzed spectra of reflected radiation, one or more analyzed frequency-shifts of reflected radiation, one or more analyzed angular degrees of reflection, one or more analyzed intensities of reflected radiation from one or more emitted wavelengths of radiation, and one or more analyzed volumetric changes of a blood vessel (BV) or tissue structure. The diagnostic software module then compares the mathematical map of the eye (E) with historical user's mathematical maps to identify a disease state of the user using one or more of the aforementioned matching algorithms. For example, early detection of pancreatic cancer is determined by the combination of: i. blood composition as determined by the second optical acquisition module and the fifth optical acquisition module; ii. a given light wave reflection pattern as determined by the fourth optical acquisition module; and iii. a given wavefront aberration map as determined by the first acquisition module. In a specific inventive embodiment, the microcontroller 24 generates a mapping identifier based on all of the map data. For example, a mapping identifier may be generated by combining, relating, and/or transforming i, ii, and iii above into a single value, range of values, or mathematical function. The diagnostic software module then cross-correlates the mapping identifier with historical user's mapping identifiers located in the master database 14 to identify a particular disease, disease state, or disease stage. It should be appreciated, that the diagnostic software module may cross-correlate remote user's analyzed optical data, mathematical maps, and/or mapping identifiers with historical user's analyzed optical data, mathematical maps, and/or mapping identifiers stored locally in the read-write memory 27 to identify a particular disease, disease state, or disease stage of the remote user in a remote location (e.g., African village) if no connectivity to the master database 14 is possible as described above.

In particular embodiments, the analyzed data, mathematical map, and/or mapping identifier of the user are transferred and stored in the master database 14 to become a component of the user's longitudinal health record and made available for diagnosing a disease state for future user's of the diagnostic eye goggle system 10. In a particular embodiment, the user repeats the data acquisition modules with the diagnostic eye goggle system 10 to track how the acquired optical data may change as a function of disease onset, disease progression, or disease regression. The tracked changes in the optical data provide incredibly valuable markers for diagnosing a disease, disease state, or disease stage of a future user of the diagnostic eye goggle system 10. The tracked changes in the optical data further provides the potential to identify disease triggering events, to aid in the diagnoses of a future diseases, or the proneness a user may be to a particular disease. By knowing how triggering events are seen from an Ophthalmological standpoint during an eye examination, several mathematical maps can be generated per disease, disease state, and disease stage for diagnosing future users with a particular disease, disease state, or disease stage.

In specific inventive embodiments, the master database 14 further receives and stores medical history data of the user linked to the user's analyzed optical data, mathematical map, and/or mapping identifier. The medical history data may include, but not limited to, a current disease state, a current disease stage, a past disease, height, weight, gender, race, smoking status, alcohol use, family medical history, blood work, and a gene map or DNA sequence of the user. The medical history data of the user and past users is stored in the master database, where the diagnostic software module cross-correlates a present user's analyzed data, mathematical map, and/or mapping identifier with historical user's analyzed data, mathematical map, and/or mapping identifier to identify a statistical match therebetween. If the diagnostic software module identifies a match, a diagnosis of one or more disease states or disease stages of the present user may be made based on the medical history of a matched historical user. For example, past user A has a medical history of Alzheimer's disease. Past user A has a specific mathematical map Y generated by the diagnostic eye goggle system 10. A new user B then utilizes the eye goggle system 10 that generates a mathematical map Z. The diagnostic software module identifies that mathematical map Y and mathematical map Z are a statistical match. The new user B may then be diagnosed with Alzheimer's disease. It should be appreciated that a user may be matched with several past user's having no diseases and thus an identification of no disease for the present user is possible. In another inventive embodiment, the analyzed optical data, mathematical maps, or mapping identifiers may be combined with genetic and other population health data in the master database, where disease analysis and triggering markers for disease initiation can be studied.

In specific embodiments, the diagnostic eye goggle system 10 further provides the user or health care provider with lens-correcting instructions or suggestions based on the analyzed wavefront data. Therefore a user receives a disease diagnosis, as well as a diagnosis of the user's visual acuity, which may be used to improve the user's visual acuity.

Figure 6:
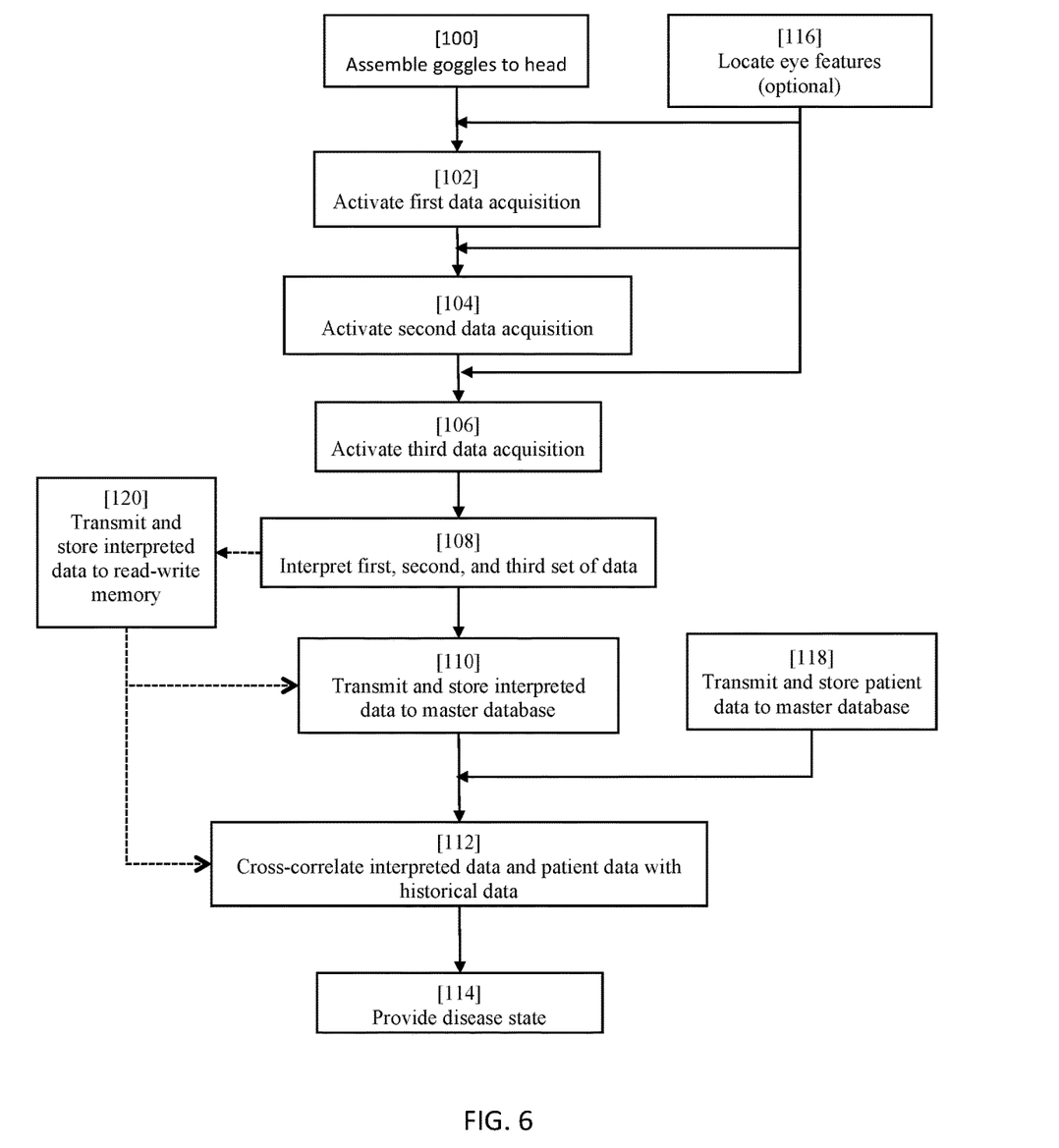
FIG. 6 depicts a method of using the diagnostic eye goggle system.

With reference to FIG. 6, a particular inventive embodiment of a method for diagnosing a disease state or disease stage of a user with the eye goggle system of claim 1 is depicted. The method includes assembling the goggles about the user's head wherein the front panel is situated in front of the user's eyes (E) [Block 100]. Emitting a first set of radiation on the user's retina with the radiation source and detecting and collecting a wavefront of reflected radiation reflected from the user's retina with the sensor [Block 102]. Emitting a second set of radiation on the user's retina with the radiation source and detecting and collecting a spectrum of reflected radiation reflected from the user's retina with the sensor [Block 104]. Emitting a third set of radiation on the user's retina with the radiation source and detecting and collecting a wavelength of reflected radiation reflected from the user's retina with the sensor [Block 106]. Generating a mathematical map of the eye (E) based on the wavefront, spectrum, and wavelength of the reflected radiation with the microcontroller 24 [Block 108]. Transmitting and storing the mathematical map of the eye (E) to a master database for diagnosing future users of the goggles [Block 110]. And, cross-correlating the mathematical map of the eye (E) with historical user's mathematical maps to provide at least one of a disease state, a disease stage, or lens-correcting suggestions to the user [Block 112]. Based on the cross-correlation as described above, a disease state is provided to the user [Block 114]. The method may further include locating one or more eye features prior to emitting at least one of the first set of radiation, the second set of radiation, or the third set of radiation [Block 116]. Medical history data of the user may also be transmitted and stored into the master database to provide historical medical data for identifying at least one of a disease state or disease stage of a future user [Block 118]. Finally, the method may include repeating the steps above at several time points for a user having a particular disease to track and store the changes of the mathematical map as a function of disease progression or regression. The tracked changes provide valuable markers to identify disease states or disease stages of a future user of the diagnostic eye goggles 10.

In another inventive embodiment, a method is provided for identifying a disease state or stage of a remote user. The goggles 12 are sent to a remote location having no connectivity to the master database 14. A first set, second set, and third set of optical eye data are acquired from a plurality of remote users at the remote location [Blocks 102, 104, 106]. The first set, second set, and third set of optical data are interpreted by a processor [Block 108] and locally stored in the read-write memory 27 locally associated with the goggles 12 [Block 120]. The interpreted data is then transmitted and stored to a master database 14 upon establishing an Internet connection between the goggles 12 and the master database 14 [Block 110]. In one embodiment, the transmitted data is then cross-correlated with historical user data stored in the master database 14 to identify at least one of a disease state and/or stage of one or more of the plurality of remote users [Block 112]. In another embodiment, the interpreted data is cross-correlated with historical user data stored in the local read-write memory 27 memory associated with the goggles 12 to identify at least one of a disease state and/or disease stage of one or more of the plurality of remote users without having to connect with the master database 14.

OTHER EMBODIMENTS

While at least one exemplary embodiment has been presented in the foregoing detail description, it should be appreciated that a vast number of variations exist. It should also be appreciated that the exemplary embodiment or exemplary embodiments are only examples, and are not intended to limit the scope, applicability, or configuration of the described embodiments in any way. It should be understood that various changes may be made in the function and arrangement of elements without departing from the scope as set forth in the appended claims and the legal equivalents thereof.

What is claimed is:

1. A diagnostic eye goggle system to identify at least one of a disease state or a disease stage of a present user, said eye goggle system comprising:
    goggles, an external master database, and a diagnostic software module executed by a processor, wherein the goggles comprise:
        one or more electromagnetic radiation sources disposed to emit radiation into one or more eyes of the user;
        one or more radiation sensors disposed to detect at least one of refraction, reflection, interference, intensity, frequency-shift, wavefront, or a spectrum of reflected radiation: reflected from one or more structures in the user's eye;
        one or more optical elements disposed between the radiation source and the radiation sensor for manipulating at least one of the emitted radiation and the reflected radiation;
        a microcontroller disposed in communication with at least one of the electromagnetic radiation source, the radiation sensor, or the optical elements, said microcontroller coordinating the emission of radiation into the user's eye, and analyzing data received from the radiation sensors; and
        a transceiver disposed in communication with the microcontroller, said transceiver forming a datalink between the microcontroller and the external master database to permit the transmission of data therebetween;
    wherein the one or more electromagnetic radiation sources, one or more radiation sensors, and one or more optical elements are self-contained in the goggles, and wherein the one or more radiation sensors are positioned in front of the present user's eye inside the goggles;
    wherein the diagnostic software module, when executed by the processor, cross-correlates a present user's analyzed data from the microcontroller with different users' analyzed data stored in the master database to determine a statistical match therebetween to identify at least one of the disease state or the disease stage of the present user; and
    wherein the different users' analyzed data includes data from at least one user having been diagnosed with a disease to permit said identification.

2. The diagnostic eye goggle system of claim 1 wherein the microcontroller comprises a processor and memory, said memory storing three or more optical data acquisition modules, said modules having software executable instructions that when executed by the processor cause the processor to acquire three or more different types of optical data from the eye.

3. The diagnostic eye goggle system of claim 2 wherein a first optical data acquisition module when executed by the processor causes the processor to: command at least one of the radiation source and optical elements to emit one or more pulses of radiation into the present user's eye, wherein a wavefront of reflected radiation is detected by the sensor and transferred to the microcontroller for eye aberration analysis.

4. The disease detecting eye goggle system of claim 3 wherein a second optical data acquisition module when executed by the processor causes the processor to: command at least one of the radiation source and optical elements to emit one or more pulses of a continuous spectrum of radiation on one or more blood vessels or tissue structures in the present user's eye, wherein a spectrum of the reflected radiation is detected by the sensor and transferred to the microcontroller for at least one of blood analyte or structure analysis of the eye.

5. The disease detecting eye goggle system of claim 4 wherein a third optical data acquisition module when executed by the processor causes the processor to: command at least one of the radiation source and optical elements to emit one or more specific wavelengths of radiation on one or more blood vessels or tissue structures in the present user's eye, wherein a frequency-shifted wavelength of reflected light is detected by the sensor and transferred to the microcontroller for at least one of analyte or structure analysis of the eye.

6. The diagnostic eye goggle system of claim 5 wherein a fourth optical data acquisition module when executed by the processor causes the processor to: command at least one of the radiation source and optical elements to emit one or more pulses of radiation at one or more target locations in the present user's eye, wherein an angular degree of reflected radiation is detected by the sensor and transferred to the microcontroller to analyze a topography of the targeted locations.

7. The diagnostic eye goggle system of claim 2 wherein the microcontroller generates a mathematical map of the present user's eye based on the analyzed data, said map having map data corresponding to an analyzed wavefront, an analyzed spectral analysis of reflected radiation, and an analyzed frequency-shift of reflected radiation combined together to form the mathematical map, wherein the mathematical map of the eye is transferred and stored in the master database, and the diagnostic software module cross-correlates the present user's mathematical map with different users' mathematical maps stored in the master database to identify a disease state of the present user.

8. The diagnostic eye goggle system of claim 7 wherein the map data corresponding to the analyzed spectral analysis of reflected radiation comprises one or more spectral line fingerprints associated with one or more blood analytes present in the present user's blood.

9. The diagnostic eye goggle system of claim 7 wherein the master database further receives and stores medical history data of the present user that is linked to the present user's mathematical map, wherein the diagnostic software module cross-correlates a present user's mathematical map with different users' mathematical maps stored in the master database to identify a statistical match therebetween, and subsequently identify at least one of the disease state or disease stage of the present user based on the medical history of a statistically matched different user.

10. The diagnostic eye goggle system of claim 9 wherein the optical elements include actuating components to actively manipulate at least one of the emitted radiation or the reflected radiation.

11. The diagnostic eye goggle system of claim 2 wherein the goggles further comprise read-write memory disposed in communication with the microcontroller, said read-write memory storing optical eye data acquired from two or more users.

12. The diagnostic eye goggle system of claim 11 wherein the read-write memory stores optical eye data acquired from two or more remote users when the datalink between the microcontroller and the external database is disconnected, wherein the transceiver transmits the optical eye data from the two or more remote users to the external master database when the datalink is restored.

13. The diagnostic eye goggle system of claim 11 wherein three or more optical data acquisition modules when executed by the processor cause the processor to: actively direct the emitted radiation to a plurality of specific locations in the present user's eye by actively adjusting one or more of the optical elements with the actuating components.

14. The diagnostic eye goggle system of claim 12 wherein the read-write memory further stores historical users' analyzed data, wherein the diagnostic software module cross-correlates the optical eye data acquired from the two or more remote users with the historical data stored in the read-write memory when the datalink between the microcontroller and the external master database is disconnected to identify at least one of a disease state or disease stage of the two or more users.

15. The diagnostic eye goggle system of claim 12 further comprising a camera disposed in the front panel and in communication with the microcontroller, said camera having an eye tracking software module for locating and tracking the pupil of the present user's eye, wherein the emitted radiation is actively directed based, in part, on a current position of the present user's pupil.

16. The diagnostic eye goggle system of claim 1 wherein the one or more electromagnetic radiation sources includes at least one of a light emitting diode (LED), a solid-state laser, an incandescent light, a fluorescent light, or a combination thereof to emit radiation in the range of 380 nanometers in wavelength to 2500 nanometers in wavelength; the one or more radiation sensors includes at least one of a charged-coupled device (CCD) sensor, a Hartmann-Shack wavefront sensor, or an array of photodiodes, or a combination thereof; and the one or more optical elements includes at least one of a slit, a pinhole, a collimator, a mirror, a beam-splitter, a lens, an x-y scanner, an x-y-z scanner, a prism, a reference arm, or a combination thereof.

17. A method for identifying at least one of a disease state or a disease stage of a present user with the diagnostic eye goggle system of claim 1, said method comprising:
    assembling the goggles about the present user's head;
    emitting a first set of radiation into the present user's eye with the radiation source;
    detecting and collecting a wavefront of reflected radiation reflected from the present user's eye with the sensor;
    emitting a second set of radiation into the present user's eye with the radiation source;
    detecting and collecting a spectrum of reflected radiation reflected from the present user's eye with the sensor;
    emitting a third set of radiation into the present user's eye with the radiation source;
    detecting and collecting a wavelength of reflected radiation reflected from the present user's eye with the sensor;
    generating, with the microcontroller, a mathematical map of the eye that combines the wavefront, spectrum, and wavelength of the reflected radiation together, wherein the mathematical map further includes data about the presence of one or more blood analytes as determined from the reflected radiation;
    transmitting and storing the mathematical map of the eye to a master database for identifying at least one of a disease state or disease stage of a future user of the goggles; and
    cross-correlating the mathematical map of the eye with different users' mathematical maps stored in the master database to identify at least one of a disease state or a disease stage of the present user.

18. The method of claim 17 further comprising:
    locating at least one of a tissue, tissue structure, or blood vessel prior to emitting at least one of the first set of radiation, the second set of radiation, or the third set of radiation; and
    transmitting and storing medical history data of the present user to the master database to identify at least one of a disease state or disease stage of a future user.

19. The method of claim 17 further comprising:
    repeating the method of claim 17 at several time points for a present user having a particular disease; and
    tracking and storing the changes of the mathematical map as a function of disease progression or regression.

* * * * *